US00PP32472P2

(12) United States Plant Patent
Lee

(10) Patent No.: US PP32,472 P2
(45) Date of Patent: Nov. 17, 2020

(54) ***GARDENIA* PLANT NAMED 'LEESIX'**

(50) Latin Name: *Gardenia hybrida*
Varietal Denomination: LEESIX

(71) Applicant: Robert Edward Lee, Independence, LA (US)

(72) Inventor: Robert Edward Lee, Independence, LA (US)

(73) Assignee: PDSI, Loxley, AL (US)

( * ) Notice: Subject to any disclaimer, the term of this patent is extended or adjusted under 35 U.S.C. 154(b) by 0 days.

(21) Appl. No.: 16/602,970

(22) Filed: Jan. 7, 2020

(51) Int. Cl.
*A01H 5/02* (2018.01)
*A01H 6/76* (2018.01)

(52) U.S. Cl.
USPC ..... Plt./255

(58) Field of Classification Search
USPC ..... Plt./226, 255
See application file for complete search history.

*Primary Examiner* — Susan McCormick Ewoldt
*Assistant Examiner* — Karen M Redden
(74) *Attorney, Agent, or Firm* — Cassandra Bright

(57) ABSTRACT

A new and distinct cultivar of *Gardenia* plant named 'LEESIX' is disclosed, characterized by uniquely profuse flowering. Foliage is narrow and glossy. Flowering will occur on a reblooming cycle Summer and Fall. Flowers are double and very fragrant. Plants are suitable for Southern climates. The new cultivar is a *Gardenia*, suitable for ornamental garden purposes.

2 Drawing Sheets

Latin name of the genus and species: *Gardenia hybrida*.
Variety denomination: 'LEESIX'.

BACKGROUND OF THE INVENTION

The new cultivar is a product of a planned breeding program by the inventor. This new variety, hereinafter referred to as 'LEESIX', was found as the result of an open pollination conducted during 2007 which included a group of unnamed, unpatented *Gardenia hybrida* plants as parents. The inventor discovered the unique seedling in Independence, La., at a research nursery during Spring of 2010.

After identifying the new variety as a potentially interesting selection, the inventor first organized propagation of 'LEESIX' by semi-hardwood cuttings during Fall of 2010 at the same nursery in Independence, La. The inventor continued confidential, controlled testing and propagation, assessing stability of the unique characteristics of this variety. Multiple generations have been reproduced and have shown that the unique features of this cultivar are stable and reproduced true to type.

SUMMARY OF THE INVENTION

The cultivar 'LEESIX' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'LEESIX' These characteristics in combination distinguish 'LEESIX' as a new and distinct *Gardenia* cultivar:

1. Distinctly profuse blooming.
2. Tolerance for environmental stress.
3. Double flowers.
4. Unique narrow leaves.

5. Very fragrant flowers.
6. Repeat blooming in Summer and Fall.
7. Good specimen plant.
8. Good container plant.

COMPARISON TO PARENT VARIETY

The parent varieties are unidentified.

COMMERCIAL COMPARISON

'LEESIX' can be compared to the commercial variety *Gardenia hybrida* 'LEETHREE', U.S. Plant Pat. No. 27,599. Plants of the new cultivar 'LEESIX' are similar to plants of 'LEETHREE' in most horticultural characteristics, however, plants of the new cultivar 'LEESIX' differ in the following:

1. 'LEESIX' has a more open, broad plant habit, compared to the round, compact plant habit of 'LEETHREE'.
2. 'LEESIX' produces double flowers, 'LEETHREE' produces single flowers.
3. 'LEESIX' flowers more profusely than 'LEETHREE'.

'LEESIX' can be compared to the commercial variety *Gardenia hybrida* 'LEETWO', U.S. Plant Pat. No. 27,601. Plants of the new cultivar 'LEESIX' are similar to plants of 'LEETWO' in most horticultural characteristics, however, plants of the new cultivar 'LEESIX' differ in the following:

1. 'LEESIX' has a more open, broad plant habit, compared to the globular, compact plant habit of 'LEETWO'.
2. 'LEESIX' produces double flowers, 'LEETWO' produces single flowers.
3. 'LEESIX' flowers more profusely than 'LEETWO'.

BRIEF DESCRIPTION OF THE PHOTOGRAPHS

Figure 1:
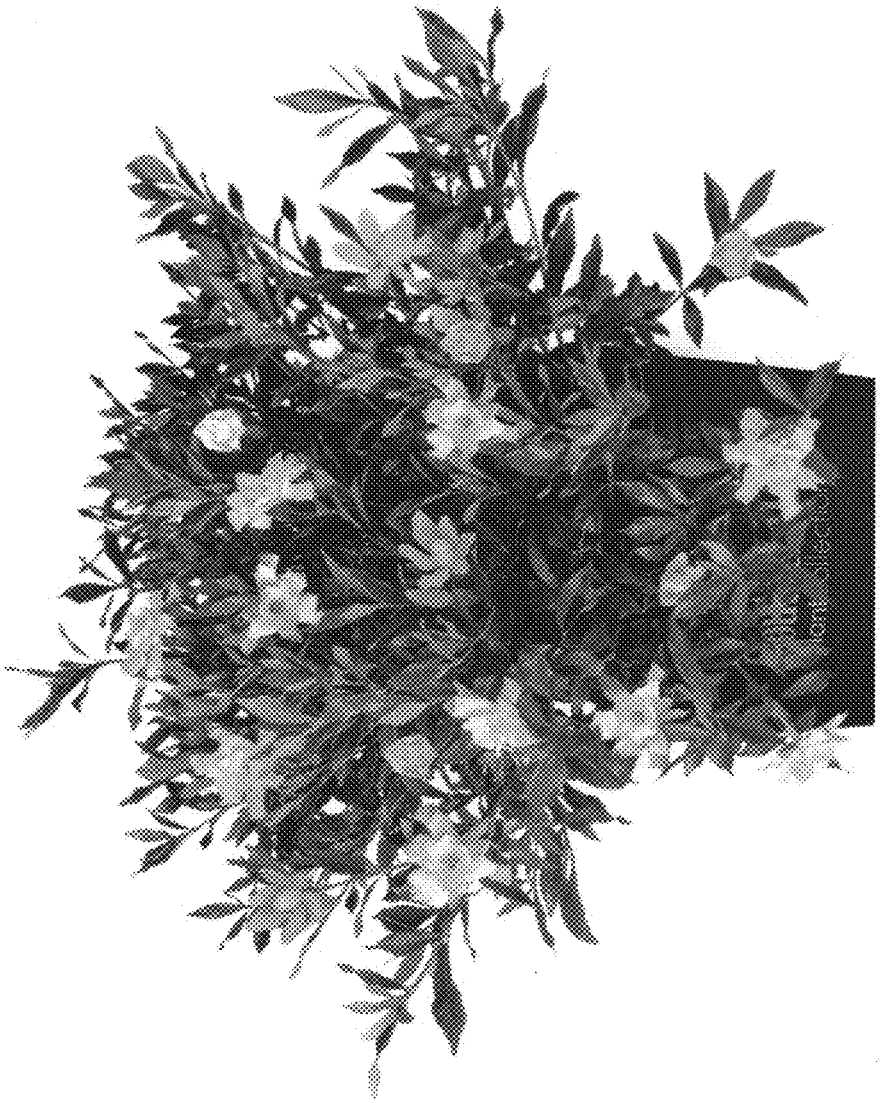

The accompanying photograph in FIG. 1 illustrates in full color a plant of 'LEESIX' grown outdoors in Alabama.

Figure 2:
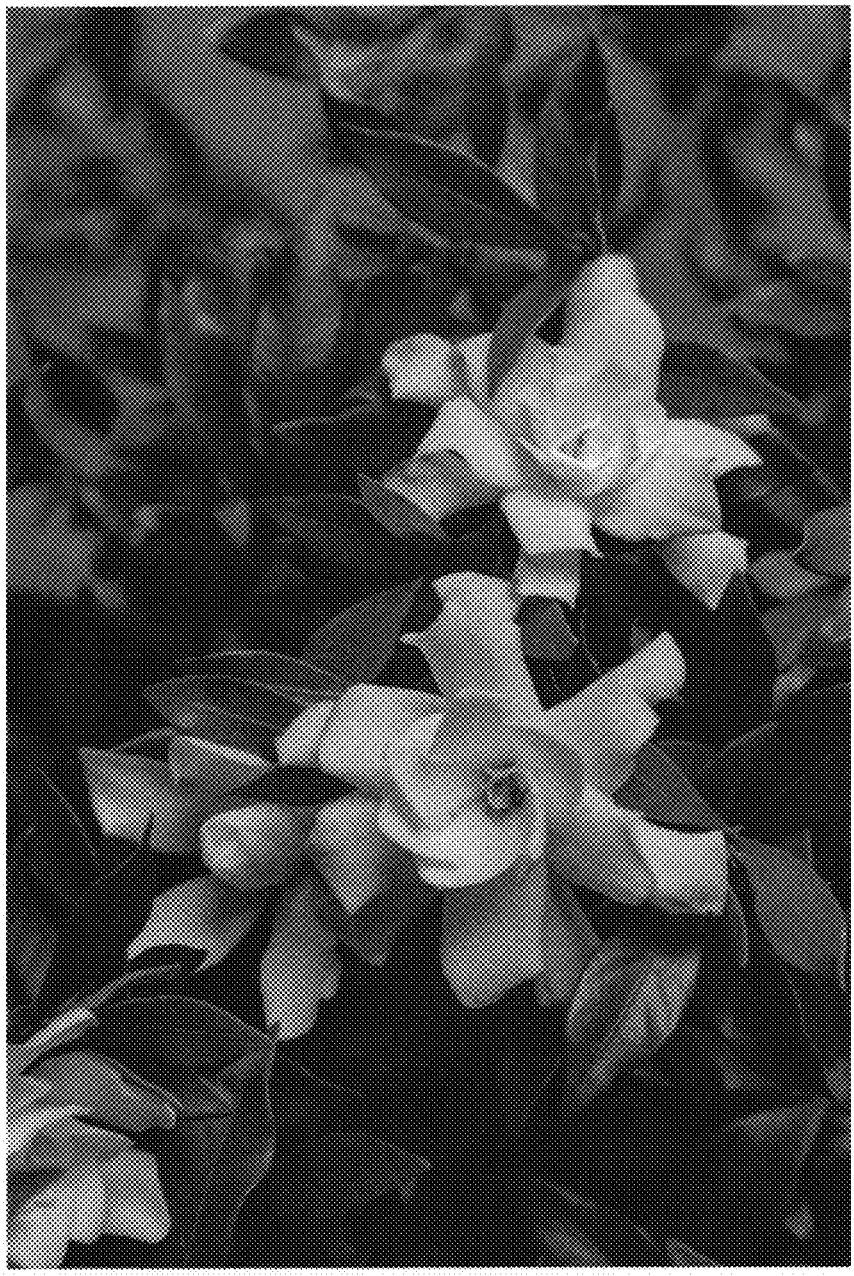

FIG. 2 shows a close up of typical flowers of the new variety. The plant is approximately 2 years old, and is shown in a three-gallon container.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'LEESIX' plants grown outdoors in Loxley, Ala. Plants are approximately 2 years old, in a 3 gallon nursery container. Measurements and numerical values represent averages of typical plant types.

Botanical classification: *Gardenia hybrida* 'LEESIX'.

PROPAGATION

Typically by semi-hardwood cuttings in Spring and Summer.

Root description: Woody to semi-wood. Colored near RHS Brown 200D.

Time to initiate roots: About 4 to 6 weeks in the Summer.

Time to produce a rooted young plant: Approximately 12 weeks in the Summer.

PLANT

Growth habit: Outwardly arching, broad globular, evergreen flowering shrub.

Height: Approximately 45 cm to top of foliar and flowering plane.

Plant spread: Approximately 65 cm.

Branching characteristics: Well branched, approximately 6 to 8 lateral branches emerge from a pinch. Smaller lateral branches occurring along main stems. Branches occur at approximately 15° to 75° angles.

Primary branches:

Length of primary branches: Average 30 cm.

Diameter of primary branches: Average range 8 to 12 mm.

Primary branch strength: Very strong, flexible, difficult to break.

Primary branch color: Near RHS Grey-Brown 199A.

Primary branch texture: Rough, nearly scaly.

Lateral branches.—

*Color*.—New growth near RHS Green 143C.

*Length*.—Average range 5 to 25 cm.

*Diameter*.—Approximately 4 mm.

*Aspect*.—Slightly curved.

*Texture*.—Rough.

*Strength*.—Strong, flexible.

*Internode*.—Average range 2.0 cm to 4.0 cm.

Age of plant described: Approximately 2 years.

FOLIAGE

Leaf:

*Type*.—Simple.

*Arrangement*.—Opposite.

*Average length*.—Approximately 4.7 cm.

*Average width*.—Approximately 1.5 cm.

*Shape of blade*.—Elliptic.

*Apex*.—Acute.

*Base*.—Broad attenuate.

*Attachment*.—Sessile.

*Margin*.—Entire.

*Internode*.—Average 2.5 cm.

*Texture of top surface*.—Glabrous.

*Texture of bottom surface*.—Glabrous.

*Appearance of top surface*.—Glossy.

*Appearance of bottom surface*.—Matte.

*Color*.—Young foliage upper side: Near RHS Green 143C. Young foliage under side: Near RHS Yellow-Green 144A. Mature foliage upper side: Near RHS Green 137A. Mature foliage under side: Near RHS Yellow-Green 144B.

*Venation*.—Type: Pinnate. Venation color upper side: Near RHS Green 138A. Venation color under side: Near RHS Yellow-Green N144D.

FLOWER

Bloom period: Plants flower in the Spring, then begin intermittent flowering cycles in late Spring/Summer through Fall.

Inflorescence:

*Arrangement*.—Double rotate flowers arise from upper leaf axils.

Peduncle:

*Length*.—Average 5 mm.

*Diameter*.—3 mm.

*Color*.—Near RHS Green 143A.

*Texture*.—Pubescent.

*Aspect*.—Straight. Angle of attachment, approximately 15° angle from stem.

*Strength*.—Moderately strong and flexible.

Flowers:

*Arrangement*.—Double rotate flowers arise from upper leaf axils.

*Length*.—Average 3.5 cm.

*Diameter*.—Average 6.5 cm.

*Facing direction*.—Outwardly and upwardly facing.

*Persistent or self-cleaning*.—Flowers persist until completely dried up, then fall off.

*Fragrance*.—Very strong, sweet fragrance.

Tube:

*Tube length*.—Approximately 2.0 cm.

*Tube width a widest point*.—Approximately 6 mm.

*Tube width and narrowest point*.—Approximately 3 mm.

Petals:

Unfused petal segments:

*Length*.—Outer whorl: Approximately 1.9 to 2.8 cm. Inner whorl: Approximately 1.0 to 1.5 cm.

*Width*.—Outer whorl: Approximately 1.0 cm. Inner whorl: Approximately 1.2 cm.

*Apex*.—Rounded.

*Base*.—Fused at base into tube.

*Shape of petal*.—Outer whorl: Unfused portion, spatulate. Inner whorl: Unfused portion, irregular orbicular.

*Petal margin*.—Entire.

*Petal arrangement*.—Rotate, outer whorl not overlapping, inner whorl overlapping.

*Petal number*.—6 outer whorl petals. 8 to 10 inner whorl petals.

*Petal texture*.—Smooth, upper and lower surfaces.

*Color*.—Upper surface at first opening: Near RHS White 155C. Under surface at first opening: Near RHS White 155C. Inner surface at maturity: Near RHS White 155C. Outer surface at maturity: Near RHS White 155C. Upper surface at fading: Near RHS White 155C. Under surface at fading: Near RHS White 155C.

Bud:

*Shape*.—Elliptic.
*Length*.—1.8 cm.
*Diameter*.—1.0 cm.
*Color*.—Near RHS White 155C swirled Yellow-Green 145B.

Calyx/sepals:

*Quantity per flower*.—6 sepals.
*Arrangement*.—Rotate.
*Shape*.—Narrow deltate, base fused.
*Length*.—Average 1.1 cm.
*Width*.—3 mm.
*Apex*.—Acute.
*Base*.—Fused.
*Margin*.—Entire.
*Texture*.—Very slightly pubescent all surfaces.
*Color*.—Inner Surface: Near RHS Green 143B. Outer Surface: Near RHS Yellow-Green 144A.

REPRODUCTIVE ORGANS

Stamens:

*Number*.—6.
*Length*.—1.
*Width*.—1 mm.
*Anthers*.—Anthers reflexed back, and attached to petals. Length: Approximately 6 mm. Width: Approximately 1 mm. Color: Near RHS Greyed-Orange N167B. Pollen: Scant, colored near Greyed-Orange 164D. Shape: Linear.

Pistil:

*Number*.—1.
*Length*.—3.2 cm.
*Style*.—Length: 2.5 cm. Color: Near RHS White 155A.
*Stigma*.—4 lobed globular, colored near 158A.
*Ovary*.—Approximately 3 mm in diameter, 4 mm long. Colored near Green-White 157A.

OTHER CHARACTERISTICS

Disease and pest resistance: Observed to be less susceptible to normal diseases and pests of *Gardenia hybrida*. Typical diseases of *Gardenia* include *Erysiphe polygoni*, and *Phomopsis gardenia*. Pests include the nematode *Meloidogyne* spp., white fly *Dialeurodes citri* and various scales, including *Ceroplastes japonicas, Icerya purchase, Fiorinia theae, Hemiberlesia rapax* and *Aspidiotus nerii*.

Temperature tolerance: USDA Zone 7 to 10.

Fruit/seed production: Not observed to date.

What is claimed is:

1. A new and distinct cultivar of *Gardenia* plant named 'LEESIX' as herein illustrated and described.

* * * * *